United States Patent [19]
Martin

[11] Patent Number: 5,639,236
[45] Date of Patent: Jun. 17, 1997

[54] ROOT CANAL DENTAL HANDPIECE

[76] Inventor: Howard Martin, 1106 Spring St., Silver Spring, Md. 20910

[21] Appl. No.: 513,732

[22] Filed: Aug. 11, 1995

[51] Int. Cl.$^6$ .................... A61C 1/10; A61C 1/12
[52] U.S. Cl. ............................. 433/131; 433/114
[58] Field of Search ..................... 433/114, 131, 433/126; 132/322

[56] References Cited

U.S. PATENT DOCUMENTS

| | | | |
|---|---|---|---|
| 1,201,363 | 10/1916 | Shelton | 433/131 |
| 3,987,549 | 10/1976 | Robertelli | 433/131 |
| 4,021,917 | 5/1977 | Nakanishi | 433/126 |
| 4,123,845 | 11/1978 | Fattaleh | 433/131 |
| 4,245,985 | 1/1981 | Eibofner et al. | 433/114 |
| 4,355,977 | 10/1982 | Ota et al. | 433/131 |
| 4,619,614 | 10/1986 | Baba et al. | 433/126 |
| 4,661,060 | 4/1987 | Strohmaier | 433/131 |
| 4,681,540 | 7/1987 | Landgraf et al. | 433/131 |
| 4,983,121 | 1/1991 | Straihammer et al. | 433/114 |
| 5,267,579 | 12/1993 | Bushberger | 132/322 |

*Primary Examiner*—Paul J. Hirsch

[57] ABSTRACT

This invention is a new handpiece for performing semi-automatic root canal procedures. The handpiece is a lightweight, low rpm, cordless and rechargeable file motor. The file is spun in a counter clockwise direction while the entire handpiece is moved in a clockwise direction. The reduction in counter torques minimize breakage of files and prepares the canal walls evenly and equally. Root canals can be performed more efficiently and effectively with this new device and method of using.

8 Claims, 1 Drawing Sheet

ROOT CANAL DENTAL HANDPIECE

BACKGROUND OF THE INVENTION

The pulp filled cavity in the root of the tooth is known as the root canal. When the pulp and the dentin on the root canal wall becomes infected, they must be removed as the infection causes severe pain for the patient. The procedure for removing the pulp and infected dentin is appropriately designated as a root canal.

The removal of the infected dentin is accomplished by use of a small cylindrical file, usually rotated within the canal manually. In performing this procedure, a skilled dentist is concerned with dual objectives: (1) debriment or cleaning of the canal and (2) shaping of the canal which helps achieve proper insertion of the obturating filling material.

Shaping of the root canal is a difficult task even for a skilled dentist as the root canal has various degrees of spatial curvatures. When shaping in these areas, it is particularly important to prevent breakage of the files within the canal, creating deviations or uneven/unequal canal wall preparations, or ledging the canal curvature. Furthermore, improper filing can lead to over preparation of the outside canal wall with under preparation of the inside canal wall in the three dimensional canal.

Even with all of the foregoing considerations when preparing the canal, most dentists still use a variation of the traditional, manual method of filing. The original manual method involves insertion of a small file into the canal, manually turning the file ¼ of a turn in the clockwise direction, followed by a withdraw. This method gives the dentist excellent tactile sensation while filing, but it has several major shortcomings. The ¼ turn is performed by rolling the file between the forefinger and the thumb. Insertion and withdraw is accomplished by wrist movements. A combination of both of these motions leads to fatigue of the dentist's hand. In addition to hand fatigue, the traditional method also does not prevent excess force form being applied against the canal wall and often a file will lock into the wall and break inside the canal. Furthermore, if the file is twisted into an unparallel angle with the canal wall when turned, it will cause unequal/uneven wall preparation which is difficult to obturate.

In an effort to overcome the "human error" associated with the precision filing of a root canal, automated dental tools were introduced. It was hoped that these automated tools would be able to simulate the ¼ clockwise turn of the traditional method. The device however did not acquire much support from the dental community for three main reasons. First, it rotated at about 3,000 rpm and often created poorly shaped canals due to an almost complete lack of tactile sensation. Second, the file frequently locks into the canal wall, causing it to break. Third, for power, it was attached to a constricting air line.

The failure of this device led to the next generation of automated root canal handpieces, ultrasonic and sonic devices using a purely reciprocal motion. The biggest draw back to these devices was the loss of tactile sense. This led to poor shaping involving elbows and alterations of the canal foramen. The sonic device led to excessive breakage of files and both instruments were restricted by being attached to air lines or special units.

The most recent development was an improvement to the automated rotating dental tool, this one rotating at almost ⅒ of the speed −350 rpms. This device rotates a full 360 degrees and is powered either by air or electricity. Again, this device compromises tactile sensation as it is large, has a restrictive cord or air line attached, and is operated by foot rheostat. The foot control has proved to be an imprecise method of regulating file rotations as evidenced by excessive file breakage.

The major failure of all mechanical handpieces is difficult to overcome as it is attributable to an inherent feature of the file. The file is supposed to cut, therefore, when rotated in the clockwise cutting direction, it has a natural tendency to catch the canal wall, stress, weaken, and then break. This result occurs more quickly if the canal is curved or the file is rotated at excessive speeds.

A variation of the traditional manual technique was implemented to overcome this inherent tendency of the file in treating the canal wall. This technique involves twisting the file in alternating clockwise and counter clockwise rotations between the forefinger and thumb when the file is inserted inside the canal. The clockwise motion sets and locks the file into the canal wall while the counter clockwise motion unthreads the file and balances the stress deformation. The major problems with this method is again breakage, due to the imprecise force applied by the dentist in the clockwise direction, and human hand fatigue and stretching of the ligaments between the thumb and forefinger of the dentist.

What is needed to overcome and improve this concept is a device which automates the counter clockwise rotation while still maintaining the clockwise insertion but in a less forceful manner to prevent file hang up and breakage and give the dentist the tactile sensation necessary to skillfully prepare the delicate root canal wall.

SUMMARY OF THE INVENTION

This invention relates to a new endodontic handpiece. More particularly this invention relates to a new endodontic handpiece that will aid in preparation of a root canal by balancing the torques in the clockwise and counterclockwise direction, minimalizing both breakage of the file and non-uniform canal wall preparation while maximizing the dentist's tactile sensation.

The key to this invention is a linear balancing of the dual countering torques applied to the file as it contacts the canal wall. This is to be accomplished by a handpiece that automatically rotates a root canal file counter clockwise while the dentist manually maneuvers the handpiece so that the rotating file rotates circumferentially around the canal wall in the clockwise cutting direction. As this device and process will not require a newly or specially designed file, the significant cutting of the canal wall occurs during the manual clockwise rotation of the handpiece. However, as the dentist rotates the file circumferentially inside the canal, the handpiece automatically rotates the file, about its own axis, in an unthreading, counter clockwise direction. The force applied on the canal wall due to the manual clockwise cutting motion is small in relation to the automatic counter clockwise rotation. Furthermore, the constant unthreading motion of the automatic counter clockwise direction will prevent the file from setting or locking into the canal wall. The minimal clockwise reaction torque and the constant unthreading automated motion almost completely obviates the problem of instrument breakage. This effect cannot be accomplished in the solely manual technique as the hand cannot continually rotate in a counterclockwise direction.

The dualling rotations allow the file to proceed with less resistance to the apex of the root. Furthermore, this device and method of use allows only light chipping of the canal wall which results in an even and equally prepared root canal. This light chipping prepares curvatures without producing deviations or elbows, or heavily cutting the canal. Since the automatic counterclockwise rotation of the file works to pull debris out of the canal, less particles are extruded through the root tip. A reduction in debris will reduce the number of inflammatory flare-ups that occur with manual or other rotary/vibratory techniques.

DETAILED DESCRIPTION OF THE DRAWINGS

Figure 1:
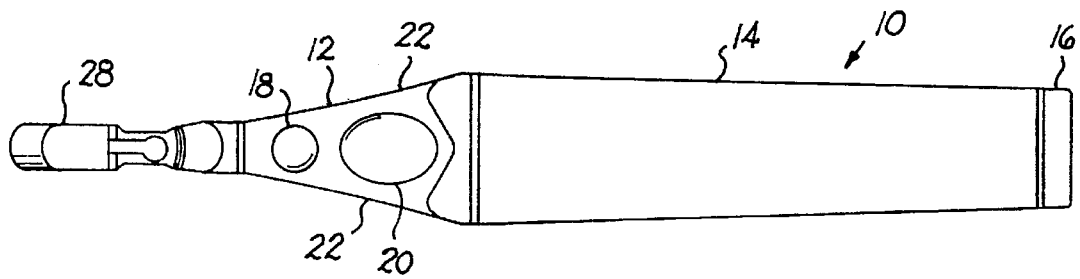
FIG. 1 is a top perspective view of the root canal device illustrating the thumb/finger depression and the on/off button.
Figure 2:
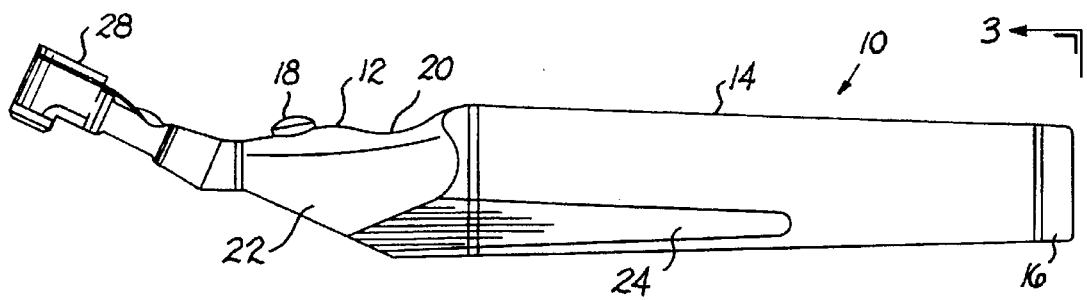
FIG. 2 is a side view of the device of FIG. 1.
Figure 3:
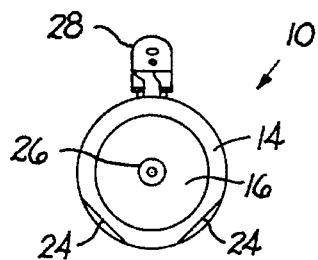
FIG. 3 is a end view of the device of FIG. 1.

The handpiece 10 associated with this new method of root canal is an integral element contributing to its success. The exterior of the handpiece 10, illustrated in FIGS. 1, 2, and 3, is constructed out of lightweight plastic or metal incorporates several indentations to aid a dentist in use and an actuator button 18. The rearward body section 14 of the handpiece 10 is substantially cylindrical and hollow. One end is capped by a rotatable selector switch 16. This switch 16 is capable of reversing the electrical circuitry within the handpiece 10 allowing the dentist to command a clockwise or counterclockwise rotation of the file. Furthermore, the rotatable selector switch 16, which also turns the unit 10 on and off, has three other selections: (1) recharging, (2) intermittent, requiring depression of the actuator button 18 to excite the motor 34, and (3) continuous, requiring no depression of the actuator button 18.

The forward body section 12 incorporates impressions within the smooth hollow section for comfort and control. Two curved sides 22 exist symmetrically on the underside of the forward body section 12. A depression 20 is located on the top portion of the forward body section. This depression 20 and dual flat portions 22 are strategically positioned to not only comfort the dentist's fingers, but to aid in performing the root canal by enhancing the tactile feel of the handpiece's 10 operation against the root canal wall. The actuator button 18 is also positioned on the top portion of the forward body section 12, slightly forward from depression 20. This positioning aids in the overall feel of the root canal and is within easy reach of a thumb or finger resting within the depression 20.

Two grooved flat portions 24 are positioned on the underside of the handpiece 10 such that they both bridge the forward 12 and rearward 14 sections. Again, these portions 24 provide a dentist with comfort and tactile sensation, while the grooves are incorporated to frictionally stabilize the dentist's grip on the handpiece 10. Overall, the body design is such that a dentist can operate the handle with a pen type grasp or a palm and thumb type grasp. The light weight and irregular shape of the handpiece 10 is specifically designed to allow the handpiece 10 to act merely as a transducer between the hand guidance and the root canal file blade.

Connected to the forward section 12 is a gear head 28. The gear head 28 is a commercial item and is well know in the art of dentist's tools. The gear head 28 secures and rotates the root canal file in a conventional manner and is removable in a conventional manner for sterilization.

Figure 4:
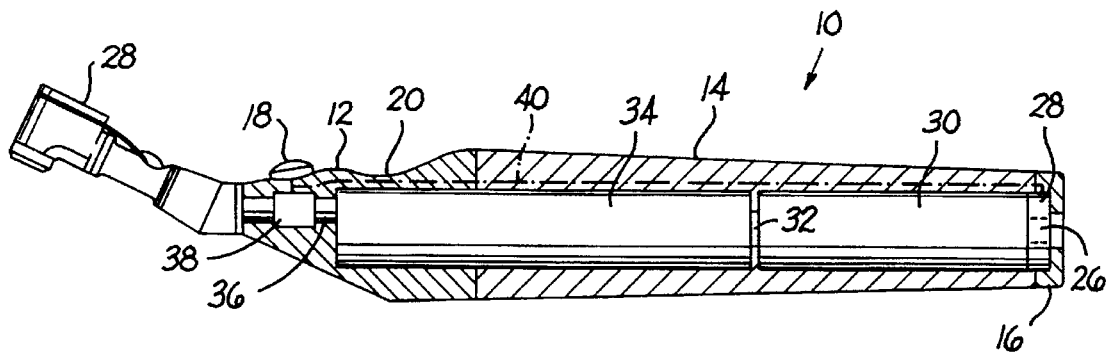
FIG. 4 is partial cross section of the root canal device illustrating the internal components.

To ensure the upmost comfort, tactile sensation and freedom of movement, this handpiece operates without a connection to an external power supply. The power for the rotational movement of the file is contained within the hollow portion of the forward 12 and rearward 14 sections. FIG. 4 illustrates the power source and its accompanying components for creating angular movement within the gear head 28 for the preferred embodiment of the invention.

The handpiece is to be powered by battery 30, leaving the handpiece free from any restrictive cords or airlines. The battery can be a typical dry cell battery purchased in any convenience store, with entry into the device accomplished by removing the rotatable selector switch 16. However, the preferred embodiment uses a rechargeable type battery 30, typically a NiCad or Alkaline, having its recharging port 26 located in the center of the rotatable selector switch 16.

The male terminal 32 of the rechargeable battery 30 resides against one end of a cylindrically configured rotating electric motor 34. The other end of the motor is connected to the negative end of the battery 30 by two separated circuits using an electrical lead 40. One of the circuits passes first through a switch 38 controlled by the external actuator button 18 and then through the intermittent position on the rotatable selector switch 16. Thus, when the selector switch 16 is rotated to intermittent, and the actuator button 18 is depressed, the circuit within the handpiece 10 is closed and the motor 34 operates.

The second circuit is for continuous operation and merely connects the motor 34 to the continuous position on the rotatable selector switch 16 such that when this switch 16 is in the continuous position, the motor 34 operates without depression of the actuator button 18. The motor 34 is connected to a shaft 36, causing the shaft 36 to angularly rotate about its longitudinal axis. The shaft 36 is connected at its other end to the interior workings of the commercial gear head 28, which converts the shaft's 36 angular velocity to file angular velocity.

An important feature of this new handpiece, is its ability to keep torsion forces acting on the file within moderate limits to prevent breakage of the file, and to consequently prepare the canal more effectively and efficiently. This is accomplished by two separate factors. First, the handpiece 10 must be operated between 350-750 rpms. The 350 rpms is associated with the handpiece 10 being used with an automated clockwise rotation. This is not the preferred embodiment. However, if the handpiece is used in this direction at this reduced speed, the reaction torque from the canal wall acting on the file is greatly reduced and helps prevent irregularities in the canal wall and breakage of the file.

The preferred embodiment, rotating the file automatically in the counterclockwise direction (the direction opposite of the file teeth), is associated with the maximum 750 revolutions per minute. This higher speed produces similarly low reaction torques as the file is spinning in the reverse or unthreading direction. Now, in order to shave the canal while the file is spinning in the reverse counterclockwise direction, the second factor is introduced. While the file is spinning counterclockwise within the root canal, the entire handpiece 10 is moved in a clockwise cyclic motion about the canal wall. The overall effect is a file spinning counter clockwise about its own longitudinal axis, while the spinning file moves clockwise in a cyclic motion about the interior circumference of the root canal wall.

The effect of the automated counterclockwise spinning is a constant unthreading rotation which prevents the file from becoming hung up on the canal wall. Additionally, this type of unthreading rotation prevents the reactionary forces due to clockwise filing from becoming large enough to stress and fracture the file blade or create problemsome irregularities in the shape of the prepared root canal.

The technique for using this method of preparing root canals is relatively simple. A dentist will gently manually insert the file into the canal and rotate it in a cyclic clockwise manner. This is done while the motor 34 of the handpiece 10 is automatically rotating the gear head 28 and file counterclockwise. In addition to constantly unthreading the file, the counterclockwise rotation automatically centers the file within the canal. The constant centering of the file will occur during bends also, so that the creation of elbows, bends, defalcations and ledges within and on the canal wall itself is avoided when using this method and handpiece.

The tactile sensation is thus retained as the dentist can feel the file against the canal wall, however, the dentist will not be able to lock the file into the wall or cut major portions of the canal wall on a single pass because of the constant unthreading automatic counterclockwise rotation of the file.

It is to be understood that the preceding detailed description of the drawings is the preferred embodiment only and that slight deviations may be made without departing from the scope of the claims.

What is claimed is:

1. A root canal handpiece, comprising:

a substantially cylindrical hollow rearward member having first and second ends;

a hollow forward member having first and second ends, said first end of said hollow forward member being fixedly connected to said second end of said rearward member;

the interior of said hollow rearward member and said hollow forward member defining a continuous extending longitudinally arranged hollow chamber therein and the exterior of said hollow rearward member and said hollow forward member defining a handle for a root canal file;

a rotatable selector switch rotatably connected to and capping said first end of said rearward member;

an internally rotatable gear head assembly having a free end for receiving said root canal file therein for rotation in a counter clockwise direction, wherein said internally rotatable gear head is removeably connected to said second end of said forward member and positioned in said hollow chamber;

power means for rotating said gear head internally, said rotating power means being contained within said hollow chamber whereby when the handpiece is rotated clockwise, said root canal file is rotated in a counter clockwise direction to obtain a more effective cutting of a root canal in a tooth.

2. A root canal handpiece as recited in claim 1, wherein said rotating power means comprises:

a rechargeable power source having positive and negative poles;

a motor having first and second ends, said second end electrically contacting said positive pole of said rechargeable power source;

a shaft fixedly connected to said gear head and said first end of said motor such that when said motor rotates said gear head internally rotates; and means for electrically wiring said motor to said negative pole of said power source whereby a closed circuit is formed therefrom.

3. A root canal dental handpiece as recited in claim 2, wherein said wiring means further comprises;

means for switching said closed circuit open or closed; and an actuation button for operating said switching means, said actuation button mounted through said forward member.

4. A root canal dental handpiece as recited in claim 3, wherein, said rotatable selector switch has at least two positions such that said wiring circuit can be continuously or intermittently closed.

5. A root canal dental handpiece as recited in claim 4, wherein, said rotatable selector switch electrically reverses said wiring means so as to allow said motor to rotate in two opposite directions.

6. A root canal dental handpiece as recited in claim 5, wherein, said hollow forward member has a pair of symmetrically positioned curves on the outer surface of said hollow forward member, said curves sloping downward from a top portion of said hollow forward member to a bottom portion of said hollow forward member;

said hollow forward member has a depression on said top portion; and said rearward and said forward members have a pair of longitudinal grooved flats, symmetrically located on the continuous outer surface of said rearward and said forward members.

7. A root canal dental handpiece as recited in claim 6, wherein, said motor rotates a file properly positioned within said gear head between 350 and 750 rotations per minute.

8. A method for performing a root canal, comprising the steps:

rotating a root canal file counterclockwise about its own longitudinal axis;

inserting said file within a root canal;

applying said file to the wall of said root canal; and moving said file in a clockwise cyclic rotation against the inner circumference of said root canal wall.

* * * * *